United States Patent [19]
Aihara et al.

[11] Patent Number: 5,287,742
[45] Date of Patent: Feb. 22, 1994

[54] DEVICE FOR DETECTING DEFECTS OF WEB

[75] Inventors: Kintaro Aihara; Shinji Yamazaki, both of Chiba, Japan

[73] Assignees: Nippon Petrochemicals Company Ltd.; Polymer Processing Research Inst., Ltd., both of Tokyo, Japan

[21] Appl. No.: 923,933
[22] PCT Filed: Jan. 10, 1992
[86] PCT No.: PCT/JP92/00013
  § 371 Date: Sep. 4, 1992
  § 102(e) Date: Sep. 4, 1992
[87] PCT Pub. No.: WO92/12410
  PCT Pub. Date: Jul. 23, 1992

[30] Foreign Application Priority Data
  Jan. 10, 1991 [JP] Japan .................. 3-12438

[51] Int. Cl.$^5$ ........................... G01D 5/28
[52] U.S. Cl. ........................ 73/159; 340/675
[58] Field of Search ............... 73/159; 340/555, 675; 250/571, 572, 221, 222.1, 562; 356/238; 26/70

[56] References Cited

U.S. PATENT DOCUMENTS

| | | | |
|---|---|---|---|
| 869,324 | 10/1907 | Obert | 73/159 |
| 1,989,971 | 2/1935 | Cretin | 340/675 |
| 2,939,963 | 6/1960 | Rideout | 73/159 |
| 3,001,080 | 9/1961 | Neil | 26/70 |
| 3,037,381 | 6/1962 | Grant et al. | 73/159 |
| 3,403,447 | 10/1968 | Taylor, Jr. | 73/159 |
| 3,800,162 | 3/1974 | Lueck et al. | 356/238 |
| 3,974,248 | 8/1976 | Atkinson | 73/159 |
| 4,063,051 | 12/1977 | Gundlach et al. | 340/675 |

FOREIGN PATENT DOCUMENTS

| | | |
|---|---|---|
| 1225550 | 12/1965 | Fed. Rep. of Germany ...... 73/159 |
| 50-20715 | 6/1975 | Japan . |
| 52-76055 | 6/1977 | Japan . |

*Primary Examiner*—William A. Cuchlinski, Jr.
*Assistant Examiner*—G. Bradley Bennett
*Attorney, Agent, or Firm*—Burns, Doane, Swecker & Mathis

[57] ABSTRACT

A plurality of probes 3 or 10 are arranged in a conveying path of a web 1 or 9 comprising a slit sheet or a nonwoven fabric for contact with the web 1 or 9. The probes 3 or 10 are rotatably supported and arranged so that if a defect portion exists in the web 1 or 9, the probes 3 or 10 rotate to the defect portion of the web and protrude under the web, and when the probes 3 or 10 protrude under the web, a detecting means 6b outputs a defect detection signal.

15 Claims, 6 Drawing Sheets

DEVICE FOR DETECTING DEFECTS OF WEB

TECHNICAL FIELD

The present invention relates to a device for detecting defects in a web, and in particular, it relates to a device for detecting defective portions, such as a portion of a tear or a portion having insufficient strength in a nonwoven fabric having a network structure or the like.

BACKGROUND ART

Recently, a variety of webs such as films or nonwoven fabrics are manufactured and used for various purposes. Defects in said webs, such as a tear (a portion at which fibers are broken) or a portion having insufficient strength, have occurred during the manufacturing process or the conveying process. To provide high quality products, it is necessary to detect such defects and remove same.

Conventionally, regarding the detection of defects in a film, there are devices for detecting defects in a film, in which light from a light emitter is irradiated on a surface of the film, and the amount of light passing through the film is measured with a detector arranged on the back side of the film. However, in conventional detecting devices, it is possible to accurately detect defects when said defects of the film exist in a relatively broad area, but it is difficult to accurately detect defects when defects of the film exist in a relatively narrow area. Also, since conventional detecting devices includes a complex means for the determination of defects, conventional detecting devices are expensive and the operation thereof is complex.

Moreover, conventionally, there are no devices for rapidly and reliably detecting defects such as tears in a web having network structures, such as nonwoven fabrics or the like. Therefore, it is necessary that the detection of defects such as tears in a web having network structures, such as nonwoven fabrics or the like, must be done by visual inspection by operators. It is therefore necessary to increase the number of operators, resulting in an increase in manpower in a manufacturing process. Also, visual inspection of defects in a high speed continuous manufacturing process results in the operators becoming fatigued thereby making it difficult to carry out a continuously accurate inspection of defects during the manufacturing process, and accordingly, the inspection of defects is carried out slowly by having to rewind the web after manufacturing the web. Therefore, an inspection of defects is not only laborious, but is also apt to result in a delay in the feedback of defect occurrence during manufacturing. Also, as it is difficult for the operators to maintain constant vigilance over a long time period of time, defects are sometimes overlooked.

SUMMARY OF THE INVENTION

The object of the present invention is to solve the above described problems of the prior art and to provide a device for detecting defects in a web by which defective portions of the web, such as tears and insufficient strength, can be reliably detected and the detection of defective portions can be carried out with less manpower and at a lower cost.

Accordingly to the present invention, there is provided a device for detecting defects in a web comprising a conveying means for conveying a web in a predetermined direction, holding means arranged near said web at least one probe rotatably pivotally attached to said holding means for making contact with the web, detecting means generating an output signal in response to the rotational movement of said probe.

With this arrangement, when the web is normal, the probe slides over the web and does not substantially rotate, and thus the detecting means does not generate a defect output signal. When a defect portion exists in the web, the probe rotates to penetrate the defect portion of the web and protrude under the web, and the detecting means generates a defect detect signal. If the detecting means generates a defect detect signal, it is possible to take the appropriate procedure. For example, it is possible to sound an alarm upon receiving a defect detect signal to request an inspection of the manufacturing process, or to indicate a defect upon receiving a defect detect signal.

Preferably, when the web to be tested comprises a laminated nonwoven fabric comprising a first web having a network structure comprising longitudinal ribbons extending generally parallel to the conveying direction and oblique ribbons extending obliquely and connected to the longitudinal ribbons, and a second web having a network structure comprising lateral ribbons extending generally perpendicular to the conveying direction, said probe comprises at least one first probe arranged so that it detects defects of said oblique ribbons between the adjacent longitudinal ribbons in the manufacturing process of said first web prior to the lamination, and at least one second probe arranged so that it detects defects of said laminated nonwoven fabric. In this case, said first probe is preferably made from a material lighter than the material of said second probe. However, in alternative arrangement, the probe can be arranged so as to detect defects in the second web only, or detect defects in the nonwoven fabric web.

BRIEF DESCRIPTION OF THE DRAWINGS

The present invention will now be described with the preferred embodiment being a specific example and with reference to the accompanying drawings, in which.

BEST MODE FOR CARRYING OUT THE INVENTION

Figure 8:
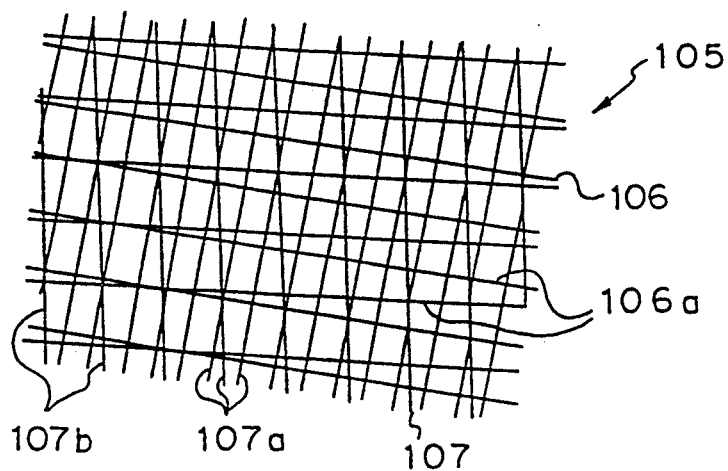
FIG. 8 is a plane view of a nonwoven fabric comprising a first web comprising lateral ribbons and a second web comprising longitudinal ribbons.

FIG. 8 shows a nonwoven fabric 105 as an example of the web to which the present invention is applied. The nonwoven fabric 105 comprises a first web 107 having a network structure comprising narrow strip-like fibriform longitudinal ribbons 107a extending like warp of a woven fabric and a second web 106 having a network structure comprising narrow strip-like fibriform lateral ribbons 106a extending like a weft of a woven fabric. The first web 107 also includes oblique ribbons 107b extending obliquely to the longitudinal ribbons 107a. This nonwoven fabric 105 is light in weight, has a high strength, is easily treated and printed, has good air permeability, is entirely homogeneous, and highly transparent, and thus is of high quality. This nonwoven fabric 105 can be used by itself as material of a reinforced net such as a drainer net, or alternatively, said nonwoven fabric 105 can be composited with various sheet material such as paper, other nonwoven fabrics or foils and used as reinforcing wrapping material.

Figure 9:
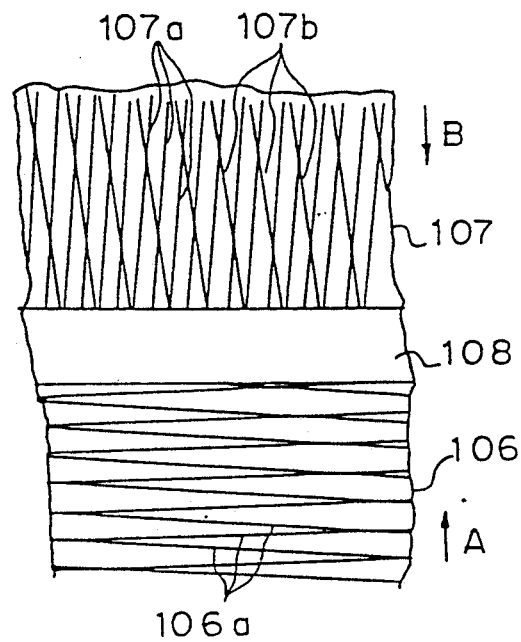
FIG. 9 is a view illustrating the formation of the nonwoven fabric of FIG. 7 by lamination.

FIG. 9 shows that the nonwoven fabric 105 of FIG. 8 is obtained by laminating the first web 107 and the second web 106 at a laminator 108. The second web 106 is conveyed toward the laminator 108 in the direction of an arrow A and the lateral ribbons 106a extend substantially perpendicular to this conveying direction. The first web 107 is conveyed toward the laminator 108 in the direction of an arrow B and the longitudinal ribbons 107a extend substantially parallel to this conveying direction. The laminated nonwoven fabric 105 rises, for example, in a direction perpendicular to the sheet in FIG. 9, and then conveyed in a direction of the arrow B.

Figure 7:
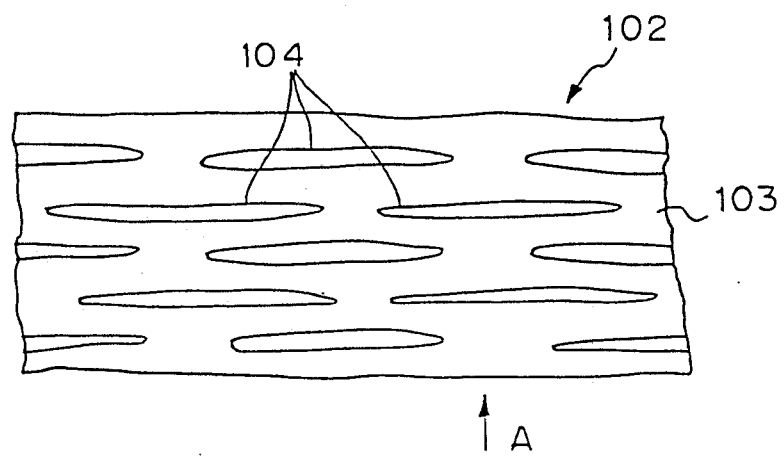
FIG. 7 is a plane view of a slit film having slits for forming a web having a network structure.

The first web 107 and the second web 106 are also called uniaxially stretched slit sheets, respectively, and obtained by forming slits in film material in a direction parallel to the arrow B and in a direction perpendicular to the arrow A, respectively, and then stretching said film materials in the direction of the slits. For example, FIG. 7 shows a slit sheet 102 for fabricating the second web 106, the slit sheet 102 comprising a film material 103 conveyed in the direction of the arrow A and slits 104 formed in a direction perpendicular to the arrow A (transverse direction to the conveying direction). The slit sheet 102 is then stretched in a direction perpendicular to the arrow A (transverse direction to the conveying direction) and it becomes the first web 106 having a network structure with lateral ribbons 106a. Similarly, the first web 107 having a network structure with longitudinal ribbons 107a and oblique ribbons 107b is obtained by a slitting process and a stretching process. Preferably, the first web 107 is obtained by stretching a film material comprising a low density polyethylene layer and a high density polyethylene layer in a direction parallel to the conveying direction, forming slits in a direction parallel to the conveying direction and in a staggered manner, and spreading the width thereof. The second web can also be made from a film material comprising low density polyethylene and high density polyethylene.

As shown in FIG. 8, the density of the longitudinal ribbons 107a of the first web 107 is considerably greater than the density of the lateral ribbons 106a of the first web 106. In addition, the oblique ribbons 107b of the first web 107 are thinner than the longitudinal ribbons 107a so that the oblique ribbons 107b are easily broken.

Also, the apparatus for manufacturing the nonwoven fabric 105 comprises continuous manufacturing processes, and it is preferable that defects of each web are detected at each process.

Figure 1:
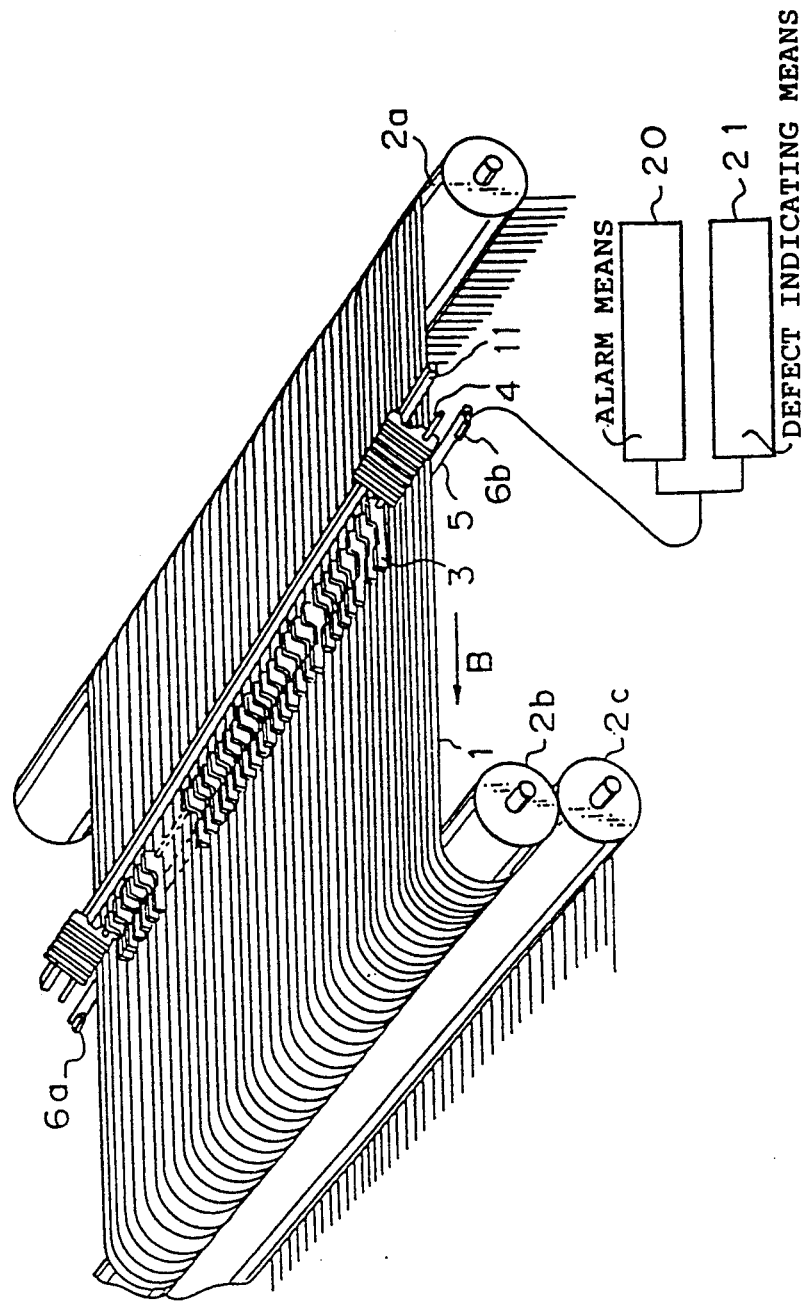
FIG. 1 is a perspective view of a device for detecting defects in a web according to the first embodiment of the present invention.
Figure 2:
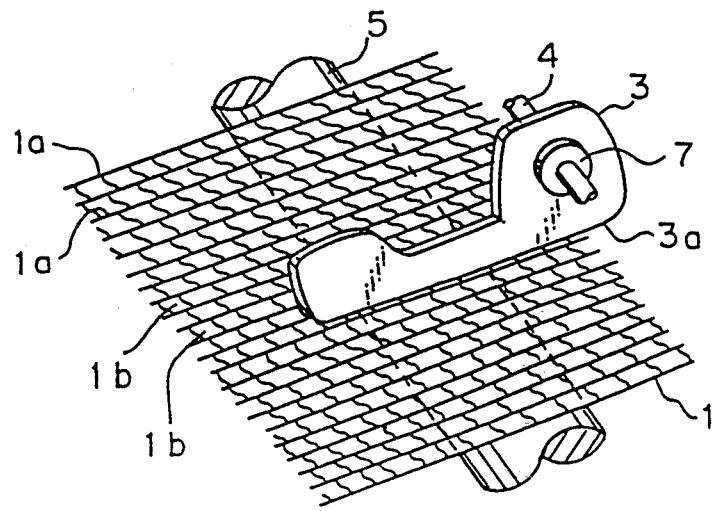
FIG. 2 is a partially enlarged perspective view of the device of FIG. 1.

A web 1 shown in FIGS. 1 and 2 corresponds to the first web 107 of FIGS. 8 and 9 (This is a web of the nonwoven fabric prior to the lamination thereof). Therefore, the web 1 has a network structure comprising longitudinal ribbons 1a and oblique ribbons 1b corresponding to longitudinal ribbons 107a and oblique ribbons 107b. In contrast, a web 9 shown in FIGS. 4 and 5 corresponds to the nonwoven fabric 105 comprising the first web 107 and the second web 106 of FIGS. 8 and 9.

Figure 3:
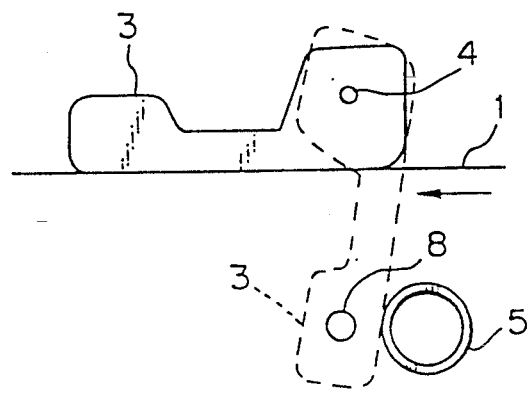
FIG. 3 is a partially enlarged perspective view of the probe of the device of FIG. 1.

Referring to FIGS. 1 to 3, the manufacturing apparatus includes conveying rollers 2a, 2b, and 2c for conveying the web 1 in the direction of the arrow B. The web 1 is generally conveyed horizontally straight by said conveying rollers 2a, 2b, and 2c. Above the web 1 are a plurality of probes 3 supported by a shaft (holding means) 4. The shaft 4 is arranged near the web 1, and preferably the shaft 4 extends transversely to the conveying direction B of the web 1 and above the web 1. The probes 3 extend parallel to the conveying direction B of the web 1.

Below the web 1 is a probe stopper pipe 5 arranged parallel to the shaft 4, and a photocoupler comprising a light emitter 6a and a light receiver (photoelectric cell) 6b is arranged at opposite ends of the probe stopper pipe 5. Said photocoupler detects defects of the web 1 in cooperation with the probes 3. The output from the light receiver 6b is connected to an alarm means 20 and a defect indicating means 21.

As shown in FIG. 2, each probe 3 is a plate-like element made from a light weight plastic material and arranged substantially parallel to the longitudinal ribbons 1a. Each probe 3a is shaped such that the length thereof is longer than an interval between the oblique ribbons 1b viewed in a longitudinal direction and has a substantially flat bottom surface 3a; the substantially whole bottom surface 3a being in contact with the web 1. That is, each probe 3 contacts several oblique ribbons 1b, and each probe 3 is pivotally attached to the shaft 4 at a position near one of the ends thereof, i.e., at a position other than the center of gravity. Each probe 3 is rested on the web 1 under the weight thereof. In addition, a probe rest bar 11 is arranged above the web 1 parallel to the shaft 4 on the upstream side of the shaft 4 in view of the conveying direction B. Therefore, it is possible for the probes 3 not in use to rest on the probe rest bar 11 to prevent the probes 3 from contacting the web 1.

A plurality of probes 3 are rotatably and pivotally attached to the shaft 4 in a row at predetermined intervals. Each probe 3 is supported immovably in an axial direction of the shaft 4 by a fastener 7. The interval between the adjacent probes 3 is preferably equal to the interval between the adjacent longitudinal ribbons 1a, or several times the interval between the adjacent longitudinal ribbons 1a, because when the oblique ribbons 1b to be detected are defective, the oblique ribbons 1b are often broken across several longitudinal ribbons 1a. In the preferred embodiment, the interval between the adjacent probes 3 is 2 to 3 millimeters while the interval between the adjacent longitudinal ribbons 1a is 4 to 5 millimeters.

With this arrangement, when the web 1 is normal, the probes 3 slide over the web 1 and do not substantially rotate, and thus the light receiver 3b does not generate a defect output signal. When a defect portion exists in the web 1, the probe 3 rotates to penetrate the defect portion of the web 1, protrude under the web 1, and abut against the probe stopper pipe 5, as shown in the broken line in FIG. 3. Accordingly, the light 8 passing from the light emitter 6a to the light receiver 6b is blocked and the light receiver 3b generates a defect detect signal. When the light receiver 3b generates a defect detect signal, the alarm means 20 sounds an alarm and the defect indicating means 21 lights a defect indicating lamp. Thus the operator can initiate the appropriate procedure on line.

In the case of the web 1 having longitudinal ribbons 1a and oblique ribbons 1b, as in this embodiment, the weight of the probe 3 is preferably determined such that the probe 3 does not damage the normal web 1, and if the web 1 is abnormal, the probe 3 rotates to penetrate the web 1, and returns again to the surface of the web 1 when the abnormality is recovered. In this regard, it is preferable that the probes 3 are made from plastic.

Figure 4:
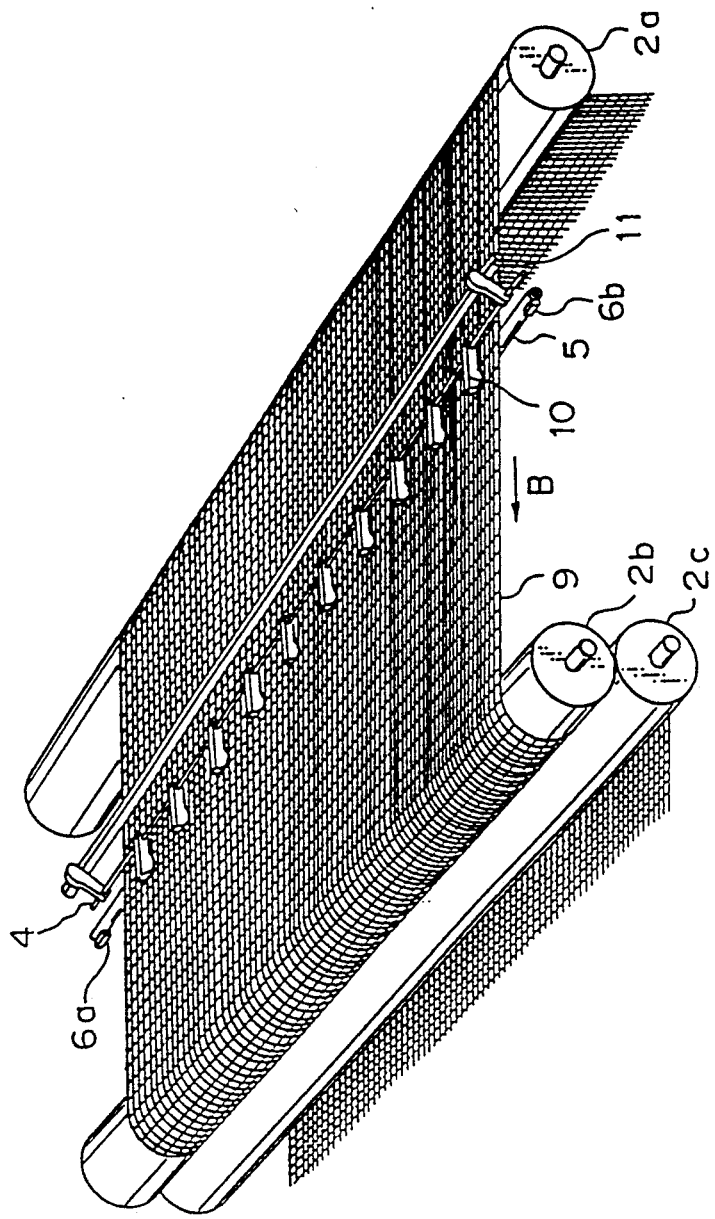
FIG. 4 is a perspective view of a device for detecting defects in a web according to the second embodiment of the present invention.
Figure 5:
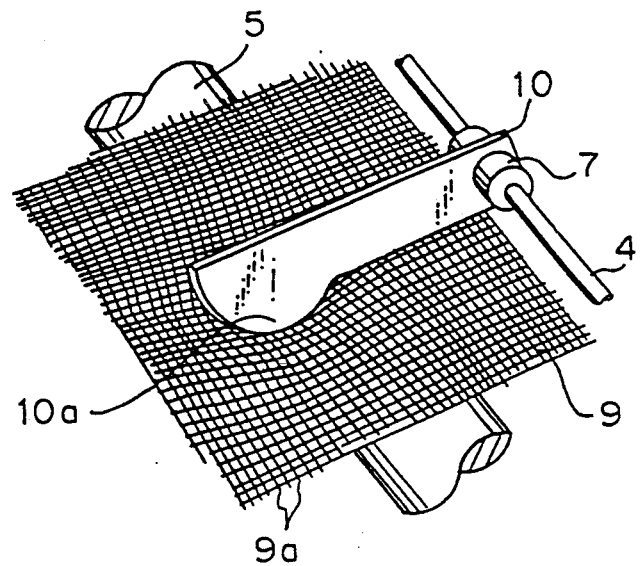
FIG. 5 is a partially enlarged perspective view of the device of FIG. 4.
Figure 6:
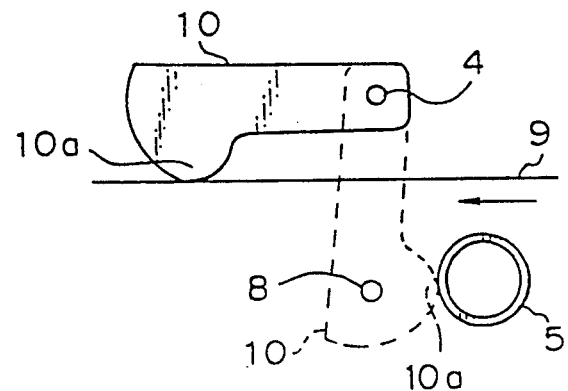
FIG. 6 is a partially enlarged perspective view of the probe of the device of FIG. 4.

FIGS. 4 to 6 show the second embodiment according to the present invention. In this embodiment, an abnormality of the nonwoven fabric 9 is mainly detected. The web 9 is generally conveyed horizontally straight by the conveying rollers 2a, 2b, and 2c. Above the web 9 are a plurality of probes 10 supported by a shaft (holding means) 4. The shaft 4 and the probe rest bar 11 are similar to the corresponding elements in FIGS. 1 to 3. Also, the probe stopper pipe 5 and the photocoupler comprising the light emitter 6a and the light receiver are arranged similarly to the previous embodiment.

A plurality of probes 10 are rotatably and pivotally attached to the shaft 4 in a row at predetermined intervals and supported immovably in the axial direction of the shaft 4 by a fastener 7, respectively. The interval between the adjacent probes 10 is greater than the interval between the probes 3 in the previous embodiment, and is approximately 20 centimeters. In addition, the probes 10 are made from steel and are heavier than the probes 3 in the previous embodiment.

The probe 10 has a lobe 10a on the bottom surface thereof at the end opposite the end thereof which is pivotally attached to the shaft 4; the lobe 10a being brought into contact with the web 9. Therefore, this probe 10 contacts the web 9 with greater contact pressure, and when a large abnormality exists in the web 9, the probe 10 rotates under the web 1, and abuts against the probe stopper pipe 5. Thereby, the probe 10 generates loud sound. In this case too, the weight of the probe 10 is preferably determined such that the probe 10 does not damage the normal web 9, and if the web 9 is abnormal, the probe 10 rotates to penetrate the web 9, and returns again to the surface of the web 9 when the abnormality is rectified.

The operation of this embodiment is substantially identical to the previous embodiment. When the web 9 is normal, the probes 10 slide over the web 9 and do not substantially rotate, and thus the light receiver 3b does not generate a defect output signal. When a defect portion exists in the web 9, the probe 10 rotates to penetrate the defect portion of the web 9, protrude under the web 9, and abut against the probe stopper pipe 5, as shown in the broken line in FIG. 6. Accordingly, the light 8 passing from the light emitter 6a to the light receiver 6b is blocked and the light receiver 3b generates a defect detect signal. When the light receiver 3b generates a defect detect signal, the alarm means 20 sounds an alarm and the defect indicating means 21 lights a defect indicating lamp. Thus the operator can initiate the appropriate procedure on line.

In addition, the web 9 can be wound in a roll. In this case, the winding machine is equipped with a labeller (not shown), which inserts a label indicating a defect, and the defect detect signal of the light receiver 3b is supplied to said labeller for insertion of the label.

Figure 10:
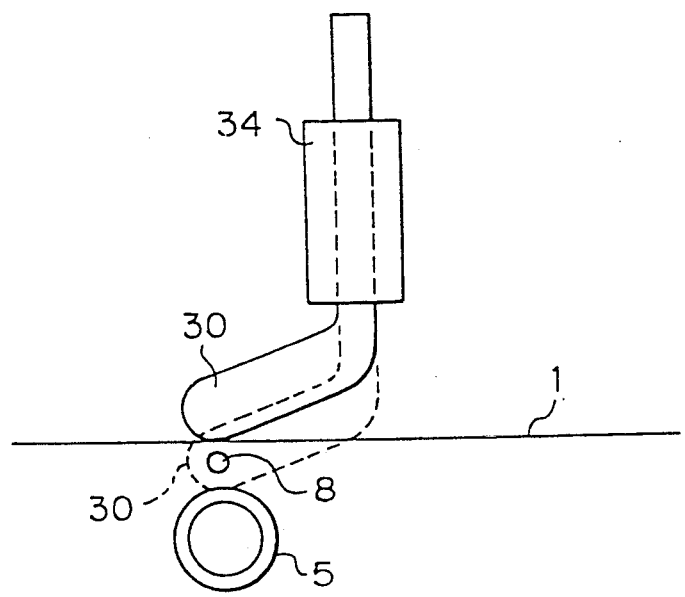
FIG. 10 is a view of another example of the probe.

The present invention has been described above with reference to the specified embodiments, but the present invention should not be limited to said embodiments. It is possible, for example, to modify and appropriately select the shape, material and disposition of the probe. Also, the probe is not limited to one that is rotatably and pivotally attached to the shaft, but it is possible to arrange the probe so as to slide. For example, FIG. 10 shows an example of a probe 30 that is slidably held so that it can slidably move from the upper surface side of the web 1 to the lower surface side. In this case, the probe 30 is slidably held by a sleeve-like holding means 34.

Also, it is possible for the probe to be brought into contact with the web under the weight thereof and also to bias the probe toward the web by a spring, a rubber, pneumatic pressure, hydraulic pressure or the like. However, it is preferable that the probe be supported at a portion other than the center of gravity and brought into contact with the web under weight, since no other biasing means is necessary.

Also, in the above described embodiments, the photocoupler is used as a detecting means for detecting the displacement of the probe, but it is also possible to use other detecting means responsive to the displacement of the probe, for example, a detecting means in which an electric current flows when the probe displaces and contacts the detecting means.

INDUSTRIAL APPLICABILITY FIELD

As explained above, it is possible, according to the present invention, to rapidly and reliably detect defective portions of the web, such as tears and insufficient strength, to thereby improve the quality and output of the products. In addition, the device for detecting defects in a web according to the present invention is a simple structure and can be manufactured at a lower cost, and operations can be carried out simply, thereby resulting in the reduction costs.

We claim:

1. A device for detecting defects in a web comprising:
   conveying means for conveying a web in a predetermined direction,
   holding means arranged near said web,
   at least one probe rotatably pivotally attached to said holding means for making contact with the web, and
   detecting means generating an output signal in response to the rotational movement of said probe,
   wherein said web comprises a laminated nonwoven fabric comprising a first web having a network structure comprising longitudinal ribbons generally extending parallel to the conveying direction and oblique ribbons extending obliquely and connected to the longitudinal ribbons, and a second web having a network structure comprising lateral ribbons generally extending perpendicular to the conveying direction; said probe comprising at least one first probe arranged so that it detects defects of the oblique ribbons between the adjacent longitudinal ribbons in a manufacturing process of said first web prior to the lamination, and at least one second probe arranged so that it detects defects of said laminated nonwoven fabric; said first probe being made of a material lighter than a material of said second probe.

2. A device for detecting defect in a web according to claim 1, wherein said web has a generally horizontal upper surface; said holding means comprising a shaft extending over said web in a direction transverse to the conveying direction of the web, and at least one probe being rotatably pivotally attached to said shaft for making contact with the upper surface of the web so that if a defect portion exists in the web, said probe rotates to penetrate the defect portion of the web and protrude under the web.

3. A device for detecting defects in a web according to claim 2, wherein said probe has a center of gravity; each of said probes being pivotally attached to said shaft at a position of the probe different from said center of gravity so that said probe contacts the web at a position of the probe on the side of the center of gravity and rotates under the weight thereof, to penetrate the defect portion in the web and protrude under the web, if the web contacts the defect portion in the web.

4. A device for detecting defects in a web according to claim 1, wherein said at least one probe comprises a plurality of probes held in a row by said holding means.

5. A device for detecting defects in a web according to claim 1, wherein said detecting means comprises a photocoupler.

6. A device for detecting defects in a web according to claim 1, wherein said device comprises an alarm means receiving the output signal from said detecting means.

7. A device for detecting defects in a web according to claim 1, wherein said device comprises a defect indicating means receiving the output signal from said detecting means.

8. A device for detecting defects in a web according to claim 1, wherein said web has a network structure comprising longitudinal ribbons generally extending parallel to the conveying direction and oblique ribbons extending obliquely and connected to the longitudinal ribbons, said probe being arranged so that it detects defects of said oblique ribbons between the adjacent longitudinal ribbons.

9. A device for detecting defects in a web according to claim 1, wherein said probe is made of plastic.

10. A device for detecting defects in a web according to claim 1, wherein said web comprises a laminated nonwoven fabric comprising a first web having a network structure comprising longitudinal ribbons generally extending parallel to the conveying direction and oblique ribbons extending obliquely and connected to the longitudinal ribbons, and a second web having a network structure comprising lateral ribbons generally extending perpendicular to the conveying direction; said probe being arranged so that it detects defects of said lateral ribbons of the second web.

11. A device for detecting defects in a web according to claim 10, wherein said probe is made of metal.

12. A device for detecting defects in a web having a plurality of ribbons extending in a longitudinal direction and a plurality of ribbons crossing said longitudinal ribbons in an oblique direction, said longitudinal ribbons being spaced from each other by a first distance and said oblique ribbons being spaced from each other by a second distance, comprising:
 conveying means for conveying the web in the longitudinal direction;
 a plurality of probes, each of said probes having a portion that has a width less than the first distance and a length greater than the second distance;
 means for holding said probes so that the probes portions extend in the longitudinal direction and so that the portion of each of said probes is brought into contact with a surface of the web so that if a defect portion exists in the web, the probe portion is displaced to an opposite side of the web, and
 detecting means for generating an output signal in response to the displacement of said probes.

13. A device for detecting defects in a web according to claim 12, wherein said holding means comprises means for pivotally holding said probes above said web, wherein said probe rotates about said holding means when the defect portion occurs.

14. A device for detecting defects in a web according to claim 12, wherein said holding means comprises a sleeve for holding each of said probes, wherein each probe is slidably disposed within its respective sleeve to enable motion in a direction substantially perpendicular to a plane of the web.

15. A device for detecting defect in a web according to claim 12, wherein said web has a generally horizontal upper surface, said holding means comprises a shaft extending over said web in a direction transverse to the conveying direction of the web, and at least one probe being rotatably pivotally attached to said shaft for making contact with the upper surface of the web so that if a defect portion exists in the web, said probe rotates to penetrate the defect portion of the web and protrude under the web.

* * * * *